United States Patent [19]

Brookfield

[11] Patent Number: 5,167,143
[45] Date of Patent: Dec. 1, 1992

[54] RHEOMETER SYSTEM

[75] Inventor: David A. Brookfield, Sharon, Mass.

[73] Assignee: Brookfield Engineering Laboratories, Inc., Stoughton, Mass.

[21] Appl. No.: 574,697

[22] Filed: Aug. 28, 1990

[51] Int. Cl.$^5$ .............................................. G01N 11/14
[52] U.S. Cl. ................................... 73/54.23; 73/54.39
[58] Field of Search ............................... 73/59, 60, 54

[56] References Cited

U.S. PATENT DOCUMENTS

| | | | |
|---|---|---|---|
| 2,074,174 | 3/1937 | Goodier | 73/60 |
| 2,133,674 | 10/1938 | Stamback | 73/60 |
| 2,573,505 | 10/1951 | Steffens | 73/60 |
| 2,713,790 | 7/1955 | Barber et al. | 73/60 |
| 2,752,778 | 7/1956 | Roberts et al. | 73/60 |
| 2,849,875 | 9/1958 | De Maria | 73/54 |
| 3,269,171 | 8/1966 | Bruss et al. | 73/60 |
| 4,154,093 | 5/1979 | Smith et al. | 73/54 |
| 4,173,142 | 11/1979 | Heinz | 73/60 |
| 4,175,425 | 11/1979 | Brookfield | 73/59 |
| 4,484,468 | 11/1984 | Gau et al. | 73/60 |
| 4,534,209 | 8/1985 | Sanders | 73/54 |
| 5,052,219 | 10/1991 | Fery et al. | 73/60 |

FOREIGN PATENT DOCUMENTS 0568869 11/1977 U.S.S.R. .............................. 73/60

Primary Examiner—Hezron E. Williams
Assistant Examiner—George M. Dombroske
Attorney, Agent, or Firm—Jerry Cohen; Edwin H. Paul

[57] ABSTRACT

Rheometric instrument with a motor (24)-driven chamber (12) and concentric spindle (14) removable for fluid changes and reinsertable between the motor drive and a transducer (30) and sense shaft 26 utilizing a flexual mount (36) and jewel—pin mount (26A) to afford repeatably precise radial and axial positioning and, as re-assembled affording a broad range of low torque to high torque response with high sensitivity and reliability and ease of fluid containment for cleaning and handling purposes.

12 Claims, 4 Drawing Sheets

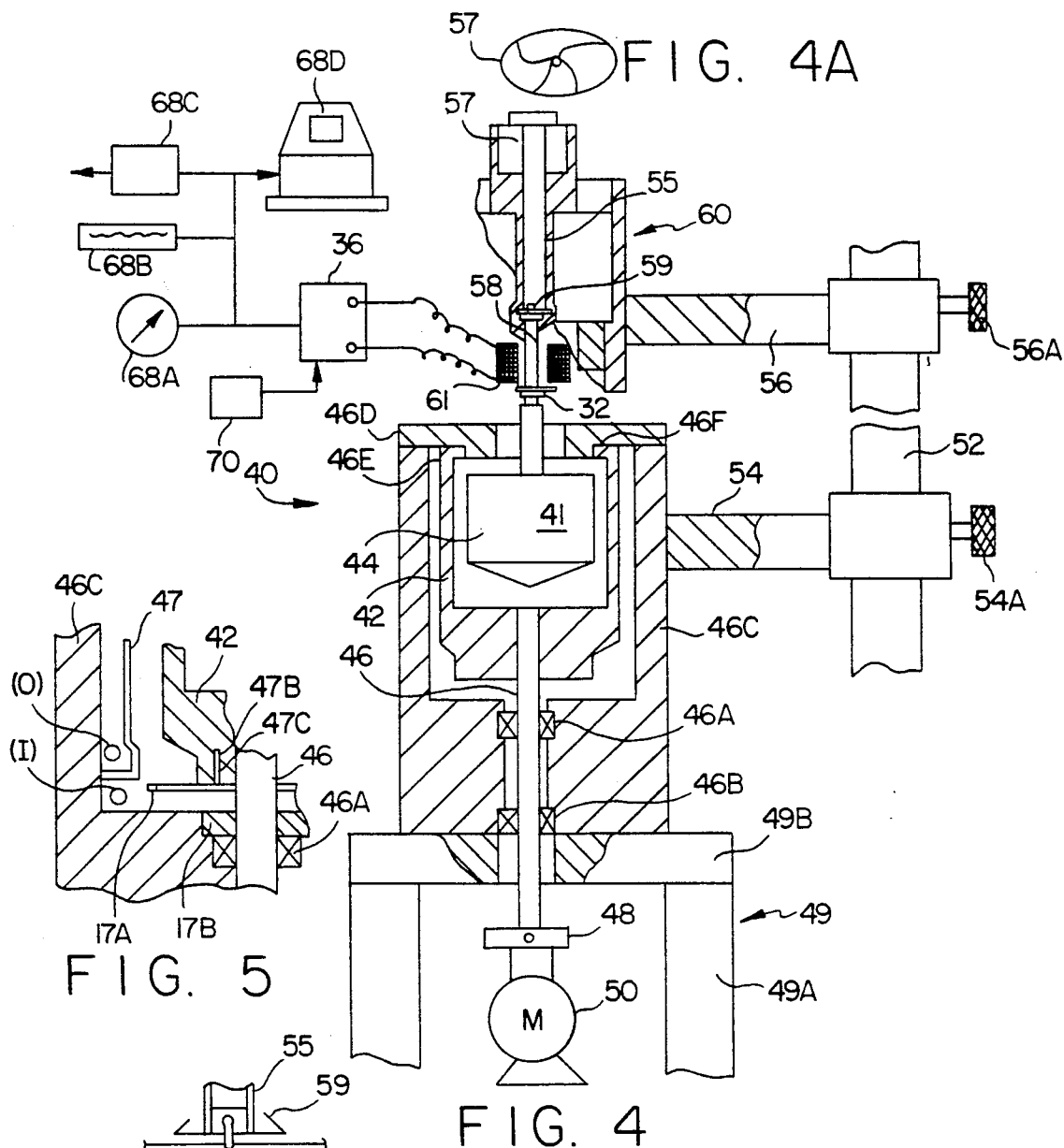
FIG. 4A
FIG. 4
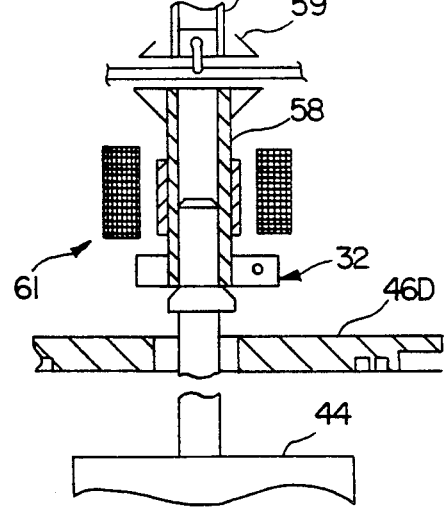
FIG. 5
FIG. 6
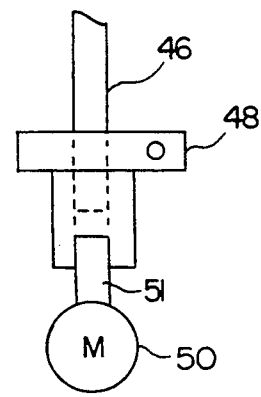
FIG. 7

RHEOMETER SYSTEM

FIELD OF THE INVENTION

The present invention relates to an instrument system for measuring rheological characteristics of fluids including single and mixed liquids, slurries, suspensions, gels, clays and finely-particulated solids and is characterized by precision, repeatability and ease of calibration and positioning adjustment through repetitive cycles of charging the system with fluid to be measured, measuring and change of fluid. The invention is also characterized by high sensitivity consistent with the above criteria.

These characteristics are realized in part through a spindle-chamber sub-assembly with precise radial and axial positioning in the system as a whole and ease of coupling-decoupling the sub-assembly consistent with other criteria stated above.

BACKGROUND OF THE INVENTION

True rheological instruments (to be distinguished from viscosity indicators) measure flow characteristics related to fluid composition, time dependent behavior, homogeneity, plasticity, yield, viscosity, all generally reduced to a read-out of a shear response as a driven member (usually a spindle) drives another member (usually a cylinder concentric to, and with a close gap relative to, the spindle) via the fluid.

These instruments have been too complex and too expensive to meet the full needs of industrial process users and laboratory users. Also, past designs have not been adaptable to the variety of tests required by users, thereby forcing the purchase of several pieces of equipment, impracticably expensive equipment, or limitations in testing capability.

SUMMARY OF THE INVENTION

It is an object of the invention to overcome the shortcomings of the prior art.

This is accomplished through instruments, in accordance with the invention which comprise spindle-chamber or other (e.g., cone-plate) sub-assembly and a related magneto-electric transducer, a torsion spring of flexural type and a jewel and pin bearing arrangement.

In some embodiments, the sub-assembly can be lifted along a guide rail for interchange of central area spindle-chamber sub-assemblies and lowered to recouple and lock the upper sub-assembly into the central sub-assembly. The arrangement, as a whole, provides reliable radial and axial positioning after such interchanges.

Other objects, features, and advantages will be apparent from the following detailed description of preferred embodiments taken in conjunction with the accompanying drawing in which:

BRIEF DESCRIPTION OF THE DRAWING

FIGS. 4 and 8 are partly sectioned side views of an instrument system made in accordance with a further preferred embodiment of the invention in closed and open positions;

FIG. 4A is a top view of a portion of a flexural, essentially frictionless pivot element of the FIG. 7-11 embodiment;

FIG. 5 is an expanded section of a portion thereof to show working elements; and FIGS. 6 and 7 are expanded views of coupling elements.

DETAILED DESCRIPTION OF PREFERRED EMBODIMENTS

Figure 1:
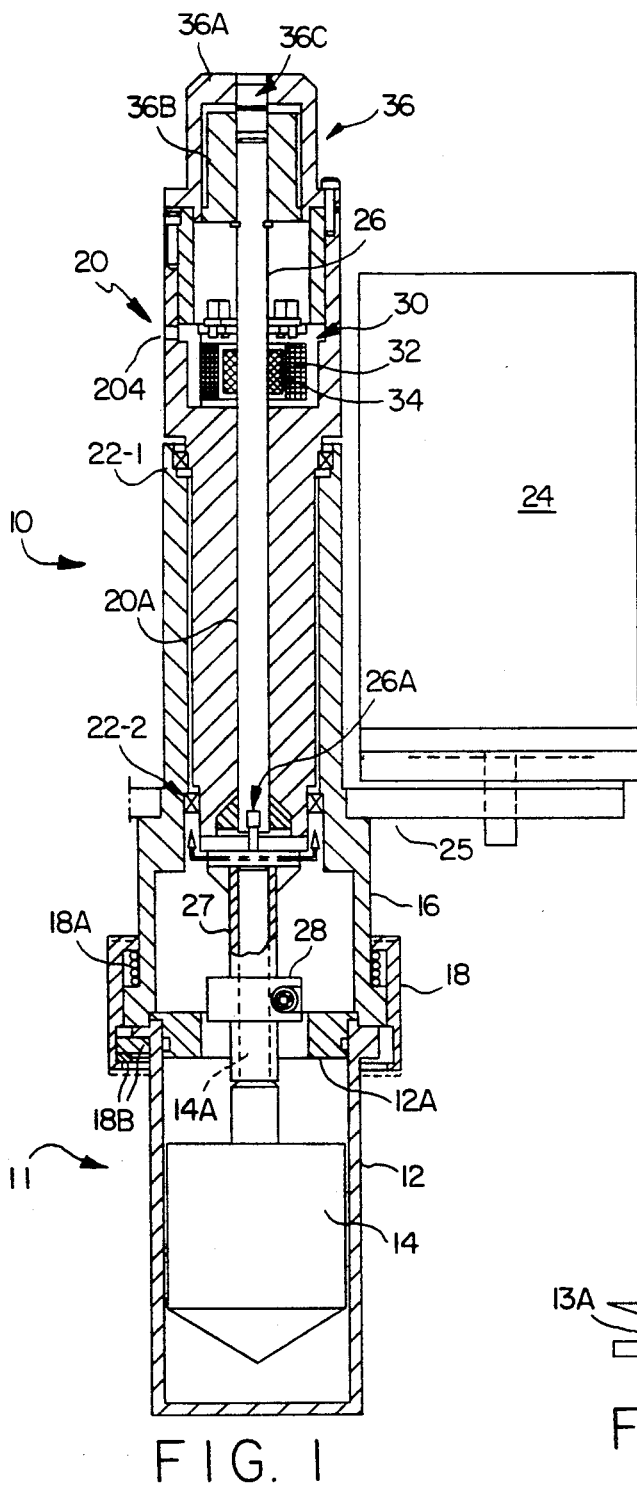
FIG. 1 is a front section view of an instrument according to a preferred embodiment of the invention.

A preferred embodiment of the invention shown in FIGS. 1-3B comprises an instrument 10 with a lower subassembly 11 including a sample chamber 12 and a spindle 14 therein defining precisely an annular region therebetween (typically 0.008"). Chamber 12 is suspended from a cylinder 16 via a demountable coupling 18 including a spring 18A and retaining detents 18B. The chamber has a cover 12A.

The cylinder 16 is mounted on a fixed structure 20 via spaced bearings 22-1 and 22-2 for rotation (and chamber 12 therewith) under drive by a motor 24 and gears 25. A sensing shaft 26 passes through a bore 20A of the fixed structure and has a lower section 27 which can be secured to shaft extension 14A of the spindle 14 via a demountable coupling 28. A pin and jewel bearing at 26A provides precise alignment of shaft extension 14A (and spindle 14 with it) and shaft 26.

A transducer 30 records shaft 26 rotary movement which is caused when motor 24 drives chamber 12 which transmits drive motion through a sample fluid therein to spindle 14 to an extent varying with viscosity of the fluid, temperature and other calibratable factors. The transducer comprises a stator 32 mounted in the fixed structure 20 and a rotor 34 secured to shaft 26. A further shaft 26 mounting is made up of a flexure pivot 36 comprising a cap 36A mounted to the fixed structure 20 and suspending, via a flexural pivot element 36C, a surrounding sleeve 36 of shaft 26.

Wiring (not shown) from the transducer 30 can pass out of fixed structure 20 via hole 20H. Conventional guards, chassis elements and other fixed structure are omitted from FIGS. 1-3B.

Successive samples are taken by loosening a bolt of coupling 28 (via a port in 18) and disconnecting chamber 12 (by compressing spring 18A and rotating connector 18 to let chamber 12 drop out along with cover 12A and spindle 14 and its shaft extension 14A). Alternatively chamber 12 can be lowered first after rotating 18 and then coupling 28 can be loosened. In either case the fluid sample in chamber 12 can be changed and the parts 12, 14 re-assembled to instrument 10 by reversing the disassembly procedure.

Throughout repeated disassembly/assembly operations, a precise recapture of the spacing of parts 12/14 is assured by the features of:

the spaced bearing elements 22-1 and 22-2 and long concentric arrangement of 16, 20, 26 between them;

the pin-jewel arrangement at 26A;

the flexural pivot 36; and the essentially lossless (i.e. no precision loss) couplings 18, 28 under the above arrangement.

This retained precise control enables an absolute reading of shear stress convertible via linear factors in instrument hardware or software to an absolute viscosity read-out, as opposed to the relative reading limitation of many conventional viscometers.

Figure 1B:
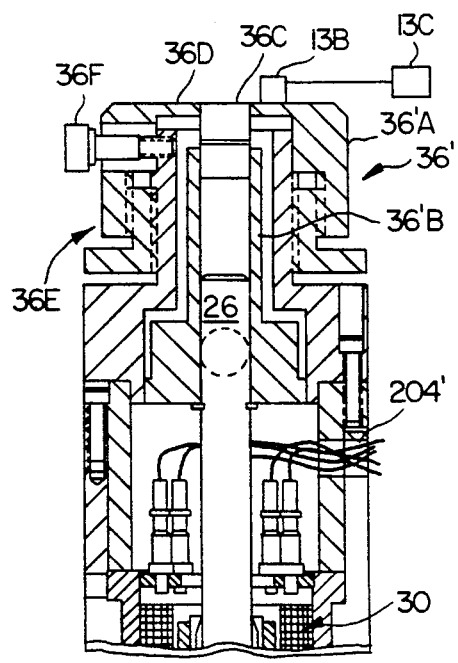
FIG. 1B is a partial front section view of the flexural mount portion of an instrument of FIG. 1 or FIG. 1A with a preferred modification.
Figure 1A:
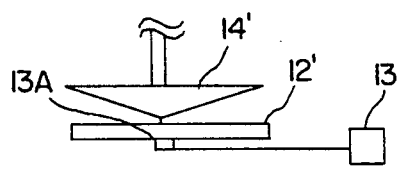
FIG. 1A is a sketch of portions of an alternate cone-plate embodiment.
Figure 2A:
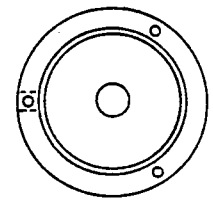
FIG. 2 is a front section view of a fixed structure component of the FIG. 1 instrument and FIGS. 2A and 2B are top and bottom views of the component.
Figure 2:
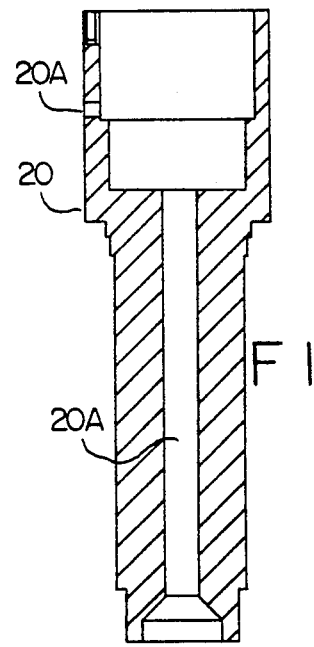
Figure 2B:
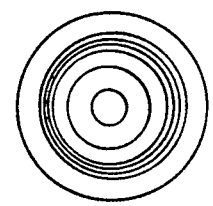
Figure 3A:
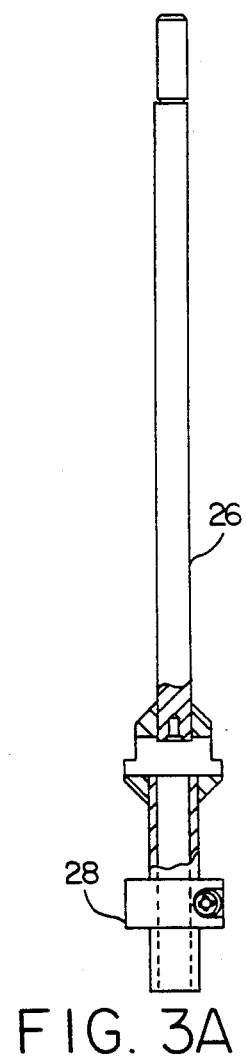
FIGS. 3 and 3A are side and bottom views and FIG. 3B a partially sectioned front view of a shaft component of the FIG. 1 embodiment.
Figure 3:
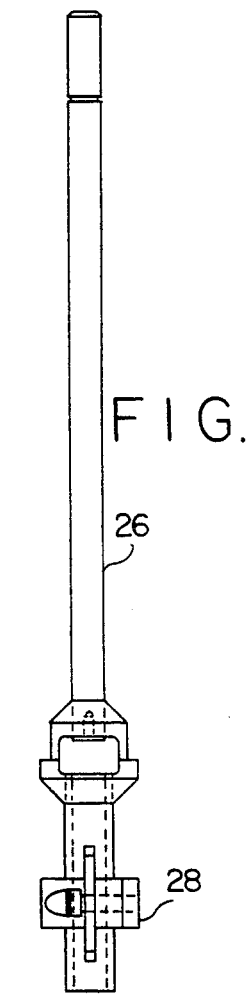
Figure 3B:
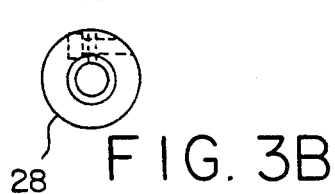

FIG. 1A shows a cone (14')-plate (12') variant of the spindle-chamber of FIG. 1, which could be mounted and operated as in FIG. 1. A supplementary transducer 13A (supplementary to main transducer 30, FIG. 1) senses force applied to the plate and a read-out via controller 13 for calibration purposes. Other variants will be apparent to those skilled in the art, e.g. parallel plate systems. In all embodiments the driving-driven relationships can be reversed.

FIG. 1B shows a further modification applicable to the FIG. 1, FIG. 1A and other embodiments for modifying the flexural mount portion. The modified flexural mount assembly 36' comprises a cap 36'A and a sleeve 36'B for suspending shaft 26 (both of 36'A and 36'B being modified compared to comparable parts 36A and 36B of FIG. 1). The flexural pivot element 36 is the same as in FIG. 1 (see also FIGS. 4 and 4A, discussed below).

The modified cap 36'A has a thin diaphragm section 36D which can be axially (i.e., shaft 26 axis) displaced by rotating a differential thread lead-screw element 36E. After such displacement, the adjusted axial position is locked in via a bolt 36F.

A supplementary transducer 13B and controller 13C provide a read-out of axial force on the diaphragm and/or displacement to assist in axial position calibration. The transducer 13B can be optical, capacitive, electro-mechanical or magnetic type, preferably capacitive.

The sleeve 36'B is dimensional to accommodate the differential thread rotary-to-axis motion device 36E within the same instrument geometric envelope as shown in FIG. 1. The device 36E can have only 1-2 turns, but because of the difference in pitch between components (typically 28 vs. 27) afford a sensitive control of axial position without fine grinding, small gear teeth or other microconstruction artifacts.

Another preferred embodiment of the invention, shown at FIGS. 4-8 comprises an instrument 40 with a central sub-assembly 41 including sample chamber 42 and a spindle 44 therein defining precisely an annular region therebetween (typically 0.008") so that clearance is established by precision dimensioning and rigidity of those parts and of related mounting parts. The chamber is mounted on a shaft 46 with spaced bearings 46A and 46B suspending the shaft in a housing 46C, that has a removable cap 46D, a lip seal 46E and an O-ring 46F. The shaft is coupled via a coupling 48 to a motor 50, the coupling and motor being contained within a housing 19 with a rigid leg or panel assembly 19A and a top 19B for support of rail 22.

Rail 52 which is mounted on support 49, provides side support and guidance for alignment via a linking arm 54 adjustable via a precision clamping screw 54A and other means described below and establishes precise spacing from the rail of the housing 46C and thereby determining the position of sample chamber 42 in relation to the spindle 44 which is similarly aligned. An upper arm 56 (with an adjusting screw 56A for positioning and for allowing sliding up/down movement or locking against such movement) extends from the rail 52 to mount an upper assembly 60 therefrom.

A flexure pivot 57 and jewel bearing 59, both described above with respect to FIGS. 1 and 1B, mount shaft 55.

The upper assembly 60 comprises a sensing shaft 58 flexure/bearing, a transducer 61 and the upper shaft 55 and associated support.

Figure 8:
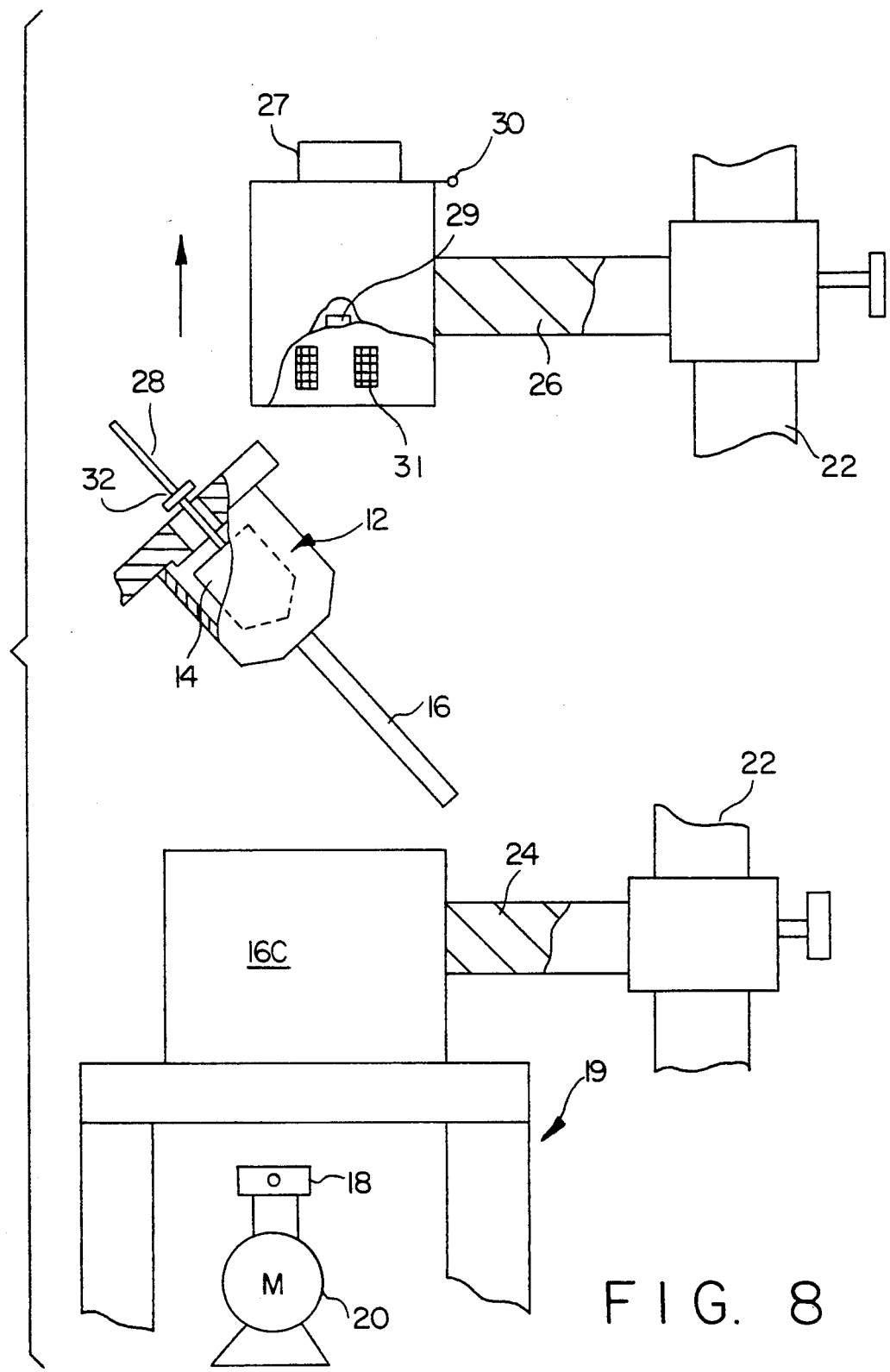

The fundamental set-up of serial measurements is that (as shown in FIG. 8) the upper sub-assembly 60 can be lifted and a central sub-assembly comprising parts 42, 44, 46, 48, 52 can be separated from the upper and lower sub-assemblies via quick disconnect couplings 48 and 52 and cap 46D of 46 is lifted from housing 46C, and removed for fluid change and then reinserted.

The instruments described above are characterized by these features of their construction and operation:

(1) Preferably the chamber 42 (not the spindle 44) is driven by motor 20. This is a stable means of shearing which minimizes eddy currents and turbulence normally occurring through spindle drive. However, in some applications, spindle drive can be employed.

(2) The rotary flexure pivot 57 coupled to a pin and jewel suspension 59, provides a minimal friction, yet assures a coaxial relation of sensor shaft 58 (and a transducer 61 rotor element thereon) within the stator coils of the transducer (a rotary variable differential transformer) as well as assuring coaxial alignment between the spindle and chamber. This arrangement provides a radial resistance but not circumferential or axial friction.

(3) The easily operated but precise mount system applied to upper and lower sections.

The cylinder 42 is preferably driven at 0 to high rpm (several thousand) by stepping motor 50 (or other good speed control motor) which provides high accuracy, speed control (typically, as in this case, 25,000 steps per revolution) and yields controlled shear rates (in conjunction with known geometry of the chamber and spindle or like elements).

The read-out from the transducer is convertible to shear stress.

Of interest here is my prior U.S. Pat. No. 4,175,425 granted Nov. 27, 1979, for a viscometer with a linear/rotary-flexural pivot and motor/belt drive-driven outer cylinder, but with the flexural pivot inside a spindle-like element and coupled thereto. Usage of flexural pivots is illustrated in U.S. patent of Merrill et al., showing a chamber supported by a rotary flexure which provides axial, radial and rotational support and is the sole support of the chamber.

As shown in FIG. 5, a divider 47 splits the annular space between chamber 42 and housing 46C into concentric paths for cooling water fed in at inlet port (I) and withdrawn at outlet port (O). When chamber 42 is removed from a collar seat 47A or shaft 46, the cooling water simply pools at the bottom of the tub defined within divider 47. A ring 47B on the collar provides a location means by slidably mating with an annular groove 47C at the bottom of chamber 42.

FIGS. 6 and 7 show the upper coupling 32 and lower coupling 18 which are essentially annular clamps, each of which can be loosened or tightened via a single screw.

The present invention affords substantial alignment improvement compared to the structures of the '425 patent and of the Merrill patent. The present invention also allows ease of change of flexure pivots for range adjustment compared to the awkwardness of access for such change in the '425 patent and the Merrill patent.

Additionally, the present invention allows for the very important use of extremely sensitive flexures for measuring thin fluids at low shear rates, which the structure of the '425 patent cannot accomplish due to the sealing tube stiffness and the structure of the Merrill patent cannot accomplish due to the requirement that the flexure support the chamber without assistance. The present invention also provides for effective fluid containment consistent with the foregoing advantages.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Rheometer system comprising:
   (a) means for defining a sample chamber surface and means for holding fluid adjacent thereto for measurement of rheological fluid properties,
   (b) means for defining an inner spindle element opposing the chamber surface and mounted to define with said chamber surface a precise gap for fluid such that relative rotation between the spindle and the chamber surface imparts a shear force from one such driving element to the other as a driven element via the fluid in the gap,
   (c) precision drive means with selectable speed for rotating at least one of the chamber surface and the spindle element at a selected, precisely defined speed,
   (d) means for defining a sensing shaft as an extension of the spindle element,
   (e) means for defining a support and torsion spring arrangement for the spindle element utilizing an axially rigid rotary spring with the sensing shaft mounted therefrom as a long shaft and further comprising a bearing at an end of the long shaft remote from the connection of the long shaft to the axially rigid rotary spring, said bearing being essentially free of axial and rotational friction and wherein said bearing provides rigid radial support to said shaft, and wherein said means absorbs the driven element's torque via the sensing shaft with a responsive spring action transmitted back to the torsion spring to yield a net deflection correlatable to the force applied by shearing of the fluid, and
   (f) transducer means responsive to rotation of the spindle element and spring action as detected at the sensing shaft to yield an output signal.

2. Rheometer system in accordance with claim 1 wherein the means (e) comprise a topmost flexural rotary spring, an elongated vertical shaft supported thereby, a jewel-pin rotational mount near the bottom of the shaft, the effective length between flexural mount and jewel-pin mount being selected to control radial driving element-driven element gap variation to within required limits to assure measurement accuracy, there being a demountable coupling between the lower end of said elongated shaft and a shaft extension of the spindle, the sensor rotor being either mounted on said elongated shaft or on an extension of the shaft's lower end but close thereto as to vary substantially less than the clearance gap between the driving and driven elements.

3. Rheometric instrument system in accordance with claim 1 wherein one of the elements is a chamber with a cover, the other a spindle, and the chamber and spindle and cover being removable via quick disconnect couplings of respective shafts extending therefrom.

4. Rheometric instrument system in accordance with claim 3 and further comprising quick disconnect means mounting upper and lower sub-assemblies for precise adjustment, the upper sub-assembly comprising said spring means and transducer means and the lower sub-assembly comprising a drive shaft of said motor means, guide means comprising guideway means and separate precision spacing means for locating the upper and lower sub-assemblies with respect to said guideway means, but allowing linear relative separation and closing movement of said upper and lower sub-assemblies for removal and insertion of said central chamber-spindle sub-assembly.

5. Rheometric instrument system in accordance with claim 1 wherein an essentially frictionless flexural mount engages the spindle.

6. Rheometric instrument system in accordance with claim 1 wherein the flexural mount is a rotary type.

7. Rheometer system in accordance with claim 4 wherein circulating fluid cooling means are provided around said chamber that do not interfere with chamber removal from and insertion into its operating position.

8. Rheometer system in accordance with claim 1 in which the system is a cone and plate type and further comprising means for adjusting the axial gap between driving and driven elements.

9. Rheometer system of claim 8 constructed and arranged such that the adjustment of the axial gap is accomplished by a differential thread mechanism for raising and lowering the cone or plate and means for detecting the point of contact between the driving and driven elements.

10. Rheometer system in accordance with claim 9 constructed and arranged such that detection of contact between driving and driven elements is accomplished by sensing the increased axial force on the driven element at and beyond contact.

11. Rheometer system in accordance with claim 10 constructed and arranged such that during operation the axial forces against the spindle and/or chamber (normal forces) are measurable by transducer means.

12. Rheometer system in accordance with claim 11 in combination with transducer means for measuring such forces.

* * * * *